United States Patent [19]

Buckle et al.

[11] Patent Number: 4,692,526
[45] Date of Patent: Sep. 8, 1987

[54] PROCESS FOR PREPARING BENZOPYRANO (2,3-D) TRIAZOLES

[75] Inventors: Derek R. Buckle; Stephen T. Carpenter, both of Redhill, England

[73] Assignee: Beecham Group PLC, Middlesex, England

[21] Appl. No.: 797,111

[22] Filed: Nov. 12, 1985

[30] Foreign Application Priority Data

Nov. 14, 1984 [GB] United Kingdom ............... 8428742

[51] Int. Cl.⁴ .......................................... C07D 413/00
[52] U.S. Cl. ................................... 544/366; 544/368; 548/256; 548/259
[58] Field of Search ............... 544/366, 368; 548/256, 548/259

[56] References Cited

U.S. PATENT DOCUMENTS 4,248,879  2/1981  Buckle et al. ...................... 548/236
4,405,620  9/1982  Buckle et al. ...................... 548/236
4,427,686  1/1984  Buckle et al. ...................... 548/236

OTHER PUBLICATIONS

Buckle et al., Chem. Abst. 96-35 265z.

Primary Examiner—Donald G. Daus
Assistant Examiner—Cecilia Shen
Attorney, Agent, or Firm—Hopgood, Calimafde, Kalil, Blaustein & Judlowe

[57] ABSTRACT

A process for preparing a compound of formula (I)

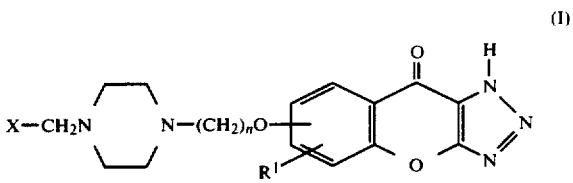

wherein X phenyl optionally substituted by one halogen, $C_{1-4}$ alkyl or $C_{1-4}$ alkoxy; or pyridyl; $R^1$ is hydrogen or $C_{1-6}$ alkyl; and n is an integer of from 1 to 6; which process comprises, cyclizing a compound of formula (II):

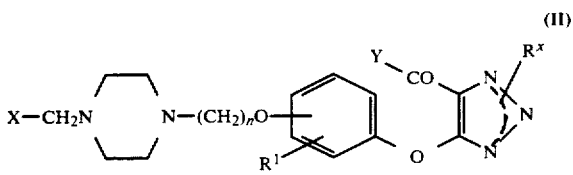

wherein X, $R^1$ and n are as defined in relation to formula (I); Y is an hydroxy or an acid activating group and $R^x$ is hydrogen or an N- protecting group and thereafter if desired carrying out one or more of the following steps: (i) removing any protecting group $R^x$, (ii) preparing a salt of the compound of formula (I).

18 Claims, No Drawings

PROCESS FOR PREPARING BENZOPYRANO (2,3-D) TRIAZOLES

The present invention relates to a novel process for preparing benzopyrano(2,3-d)triazole derivatives and to novel compounds useful as intermediates therein.

European Pat. No. 0,034,004 discloses compounds of formula (I) and their use in therapy:

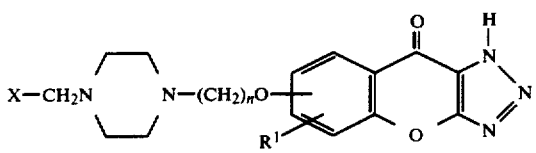

(I)

wherein X is phenyl optionally substituted by one halogen, $C_{1-4}$ alkyl or $C_{1-4}$ alkoxy; or pyridyl; $R^1$ is hydrogen or $C_{1-6}$ alkyl; and n is 1 to 6.

We have discovered a novel process for preparing such compounds.

Accordingly the present invention provides a process for the preparation of a compound of formula (I) as hereinbefore defined or a pharmaceutically acceptable salt thereof; which process comprises, cyclising a compound of formula (II):

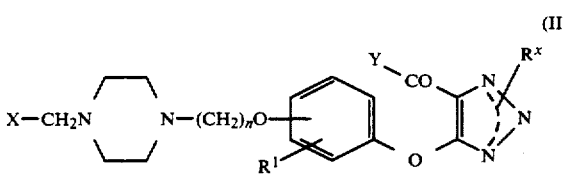

(II)

wherein X, $R^1$ and n are as defined in relation to formula (I); Y is an hydroxy or an acid activating group and $R^x$ is hydrogen or an N-protecting group and thereafter if desired carrying out one or more of the following steps: (i) removing any protecting group $R^x$, (ii) preparing a salt of the compound of formula (I).

Suitable examples of N-protecting groups $R^x$ are labile benzyl groups, for example $C_{1-6}$ alkoxy substituted benzyl groups. One particularly suitable example of $R^x$ is 4-methoxybenzyl.

Suitable activating groups for Y include those whereby the group —COY is an acid halide or anhydride.

Preferably Y is halide such as chloride.

Preferred groups for X, $R^1$ and values for n in the compound of formula (II) are the same as those employed in formula (I) as outlined hereinafter and in European Pat. No. 0,034,004.

In a preferred aspect of the invention, the cyclisation of the compound of formula (II) where Y is an acid activating group, is carried out in the presence of an effective Lewis acid such as aluminium trichloride and/or a $C_{1-6}$ alkyl aluminium dichloride.

Preferably the Lewis acid is one which will remove any N-protecting group $R^x$ during the cyclisation step.

Suitably the cyclisation of a compound of formula (II) where Y is an acid activating group is carried out in the presence of a $C_{1-6}$ alkyl aluminium dichloride. A preferred $C_{1-6}$ alkyl aluminium dichloride is ethyl aluminium dichloride.

Suitably, when a $C_{1-6}$ alkyl aluminium dichloride is used the reaction is carried out within the temperature range of 0° C. to 30° C.

Preferably the $C_{1-6}$ alkyl aluminium dichloride is added to the compound of formula (II).

Preferably the $C_{1-6}$ alkyl aluminium dichloride is dissolved in an inert organic solvent such as n-hexane Suitably the cyclisation of a compound of formula (II) where Y an acid activating group is carried out in the presence of aluminium trichloride. Aluminium trichloride will also be effective to remove a protecting group $R^x$ where this group is a labile benzyl group as described above.

The reaction may be carried out in any suitable inert organic solvent, such as dichloromethane, within a temperature range of −30° C. to 30° C.

Suitably when aluminium trichloride is used the reaction is carried out within the temperature range of −30° C. to 10° C.

Alternatively cyclisation of a compound of formula (II) where Y is hydroxy can be carried out by treatment with a dehydrating agent such as polyphosphoric acid or methanesulphonic acid containing phosphorus pentoxide.

The reaction is suitably carried out at an elevated temperature of for example from 40° to 110° C., preferably under an inert atmosphere of for example nitrogen.

When necessary, the protecting group $R^x$ may be removed in any convenient way which does not disrupt any other part of the molecule. For example we have found that acid catalysis is generally suitable. It is preferable to use the p-methoxybenzyl protecting group which is readily removed using trifluoroacetic acid, the course of the cleavage being followed by high pressure liquid chromatography or by NMR spectroscopy. Suitably temperatures of around 30° C. to 70° C. can be used, with a suitable reaction time of between 3 to 12 hours. Other strong acids such as methanesulphonic acid behave similarly.

The compounds of formula (II) as hereinbefore defined are novel and as such form an aspect of the invention.

The compounds of formula (II) wherein Y is an acid activating group can be prepared by reacting a compound of formula (II) wherein Y is hydroxy with a conventional activating reagent.

For example, Y can be converted from hydroxy to halide by treatment with an acid chloride such as oxalyl chloride or thionyl chloride, preferably oxalyl chloride.

The reaction may be carried out in any suitable organic solvent, such as dichloromethane, at ambient or slightly depressed temperatures. Preferably the reaction is carried out in the presence of an N.N-dimethylformamide catalyst.

The compounds of formula (II) wherein Y is hydroxy may be prepared by de-esterification of an ester of formula (III)

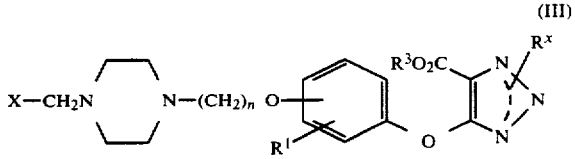

(III)

wherein X, $R^1$, $R^x$ and n are as defined in relation to formula (II) and $R^3$ is $C_{1-6}$ alkyl, such as ethyl; or benzyl.

Suitably the reaction is carried out in alkaline conditions, for example by treatment of a compound of formula (III) with sodium hydroxide, in any suitable solvent, such as aqueous ethanol at a temperature of between 0° C. and 50° C., preferably at room temperature.

The intermediate esters of formula (III) are novel compounds and as such form a further aspect of the present invention.

The compounds of formula (III) may be prepared by reaction of a salt, preferably an alkali metal salt, of a compound of formula (IV):

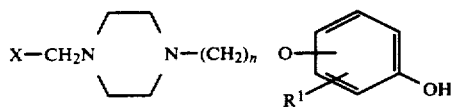

(IV)

wherein X, $R^1$ and n are as defined in relation to formula (I), with a compound of formula (V):

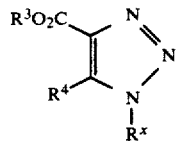

(V)

wherein $R^3$ and $R^x$ are as defined in relation to formula (III), and $R^4$ is a leaving group.

A preferred salt of a compound of formula (IV) is a sodium salt.

Suitably $R^4$ is halogen preferably chlorine.

Suitably the reaction is carried out by treating the compound of formula (IV) with a metal hydride, preferably an alkali metal hydride, such as sodium hydride, in an aprotic solvent such as dimethyl formamide, and then reacting the salt so formed with the compound of formula (V) at ambient or elevated temperature of for example from 40° C. to 100° C. The compounds of formula (IV) may be prepared by reacting a compound of formula (VI):

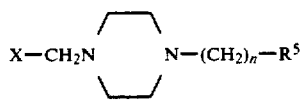

(VI)

wherein X and n are as defined in relation to formula (I) and $R^5$ is a leaving group such as tosyloxy, mesyloxy or halogen, with a compound of formula (VII):

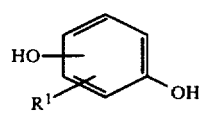

(VII)

wherein $R^1$ is as defined in relation to formula (I).

Preferably $R^5$ is chlorine.

The reaction is generally carried out in the presence of a moderate base in a polar solvent. Examples of suitable bases include basic alkali metal salts such as the carbonates, for instance potassium carbonate.

Examples of suitable solvents include ketones; such as butanone.

The reaction is conveniently carried out under reflux at temperatures of 50° to 110° C. depending on the solvent, base and particular starting materials employed.

The compounds of formula (V), (VI) and (VII) are either known compounds or may be prepared by analogous methods to known compounds, for example as described in European Pat. No. 0,034,004.

The above described process can suitably be employed to produce compounds of formula (I) where X is an optionally substituted phenyl group, represented by:

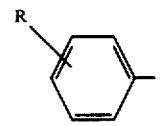

wherein R is hydrogen, halogen, $C_{1-6}$ alkyl or $C_{1-6}$ alkoxy. Suitable examples of R include hydrogen, fluorine, chlorine, bromine, methyl, ethyl, methoxy and ethoxy. More suitably R is hydrogen or halogen, preferably chlorine. Preferably R, when halogen, is in the o- or p-position and most preferably p-chloro.

Alternatively X may be pyridyl. In such cases X is suitably 2- or 4-pyridyl, preferably 2-pyridyl.

Suitable examples of $R^1$ include hydrogen, methyl, ethyl and n- and iso-propyl. When other than hydrogen, $R^1$ is suitably in the 5-position (that is, substituting the carbon atom adjacent the oxygen atom joined bridgehead carbon atom). Preferably $R^1$ is hydrogen or 5-methyl. n is suitably 2, 3 or 4, preferably 3.

The side chain oxygen atom may join the benzopyrano[2,3-d]-1,2,3-triazole nucleus at any non-bridgehead carbon in the benzo moiety. Suitably however it will be joined at the 6-position (that is, substituting the carbon atom meta- to the oxygen atom joined bridgehead carbon atom).

Within formula (I) there is a group of compounds of formula (I)′:

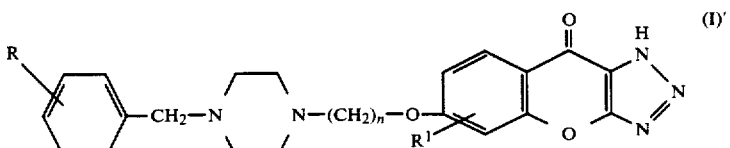

(I)′ wherein R is hydrogen, halogen, $C_{1-4}$ alkyl or $C_{1-4}$ alkoxy; $R^1$ is hydrogen or $C_{1-6}$ alkyl; and n is 1 to 6.

Suitable and preferred examples of the variable groups therein are as described in relation to formula (I).

Within formula (I) there is also a group of compounds of formula (I)'':

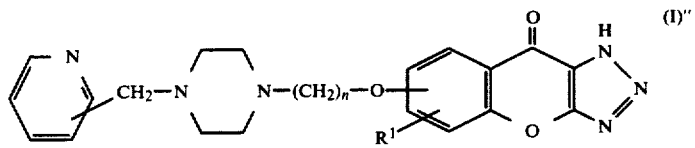

wherein R$^1$ is hydrogen or C$_{1-6}$ alkyl; and n is 1 to 6.

Suitable and preferred examples of the variable groups therein are as described in relation to formula (I).

From the aforesaid it will be appreciated, that one preferred sub-group of compounds of the formula (I) is of formula (I)''':

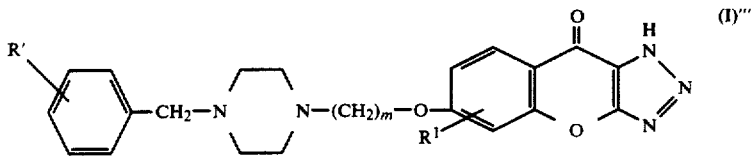

wherein R' is hydrogen or halogen, R$^1$ is hydrogen or C$_{1-6}$ alkyl, and m is 2, 3 or 4.

Suitable and preferred values for R', R$^1$ and m are as herinbefore described for R, R$^1$ and n respectively.

Thus R' when halogen is preferably in the o- or p position, most preferably p-chloro.

Similarly R$^1$ when alkyl is preferably in the 5-position, preferably hydrogen or 5-methyl.

A particularly preferred compound of formula (I) is 6-{3-[4-(4-chlorobenzyl)-1-piperazinyl]-propoxy}-9-oxo-1H,9H-benzopyrano[2,3-d]-1,2,3-triazole.

The following Examples illustrate the present invention.

EXAMPLE 1

1-[4-(4-Chlorobenzyl)piperazin-1-yl]-3-(3-hydroxyphenoxy)propane

To a solution of 1-chloro-3-[4-(4-chlorobenzyl)piperazin-1-yl]propane (50 g, 0.174 mole, prepared as in EP No. 10392) in butanone (250 ml) was added sodium iodide (26.09 g, 0.174 mole) and the mixture was stirred for 45 minutes under N$_2$. This solution was then added dropwise to a stirred, refluxing mixture of resorcinol (95.84 g, 0.87 mole), anhydrous potassium carbonate (24.06 g, 0.174 mole) and butanone (400 ml) which had previously been heated to reflux for 1.5 hours. After a further 26 hours at reflux the mixture was cooled and filtered. Concentration in vacuo afforded a brown oil which was redissolved in ethanol (500 ml) and acidified with ethanolic hydrogen chloride (400 ml). The resulting precipitate was filtered off under N$_2$, washed with ethanol and dissolved in water (1.25 liters) at 50° C. Saturated aqueous sodium bicarbonate solution was added to pH 7 and the product extracted into dichloromethane. Evaporation of the dried extracts gave a white solid which on trituration with ether gave 45.82 g (73%) of the title compound of mp (EtOH) 134°–135° C., $\nu_{max}$(KBr) 1490, 1600, 2820, 2870, 2940, 3420 cm$^{-1}$, δ(DMSO) 1.98 (2H, m, CH$_2$CH$_2$CH$_2$), 2.56 (8H, bs, N—CH$_2$ [piperazine]), 2.6 (2H, t, N—CH$_2$), 3.48 (2H, s, CH$_2$Ar), 3.92 (2H, t, J=6 Hz, O—CH$_2$), 5.6 (1H, broad exchangeable, OH), 6.32–6.41 (3H, m, aromatic), 7.06 (1H, t, J=8 Hz, resorcinol C—5H), 7.25 (4H, d,d, J=13 Hz, 8.5 Hz, chlorobenzyl aromatic).

Found; C, 66.40; H, 7.07; N, 7.66; Cl, 10.14; C$_{20}$H$_{25}$ClN$_2$O$_2$ requires; C, 66.56; H, 6.98; N, 7.76; Cl, 9.83%.

EXAMPLE 2

Ethyl 5-{3-{3-[4-(4-chlorobenzyl)-1-piperazinyl]propoxy}phenoxy}-1-(4-methoxybenzyl)-1,2,3-triazole-4-carboxylate A solution of 1-[4-(4-chlorobenzyl)piperazin-1-yl]-3-(3-hydroxyphenoxy)propane (7.00 g, 0.019 mole), in dry dimethyl formamide, (200 ml) was treated portionwise with 60% sodium hydride in oil, (0.776 g, 0.019 mole), under a slow stream of nitrogen. The mixture was stirred at room temperature for 0.5 h, then Ethyl 5-chloro-1-(4-methoxybenzyl)-1,2,3-triazole 4-carboxylate (5.74 g, 0.019 mole) was added. The reaction was stirred at 100° C. for 24 hours, then cooled and the solvent removed in vacuo. The brown residue was partitioned between ethyl acetate and water and the organic phase separated, washed with water (twice), and dried, (MgSO$_4$). Evaporation in vacuo gave the crude product as a pale brown oil which was purified by column chromatography to yield 8.52 g (72%) of the title compound as a pale yellow oil. $\nu_{max}$ (film) 1510, 1560, 1590, 1615, 1730, 2810, 2940 cm$^{-1}$ δ(CDCl$_3$) 1.11 (3H, t, J 7 Hz, ester CH$_3$), 1.91 (2H, m, CH$_2$), 2.51 (10H, piperazinyl+CH$_2$), 3.46 (2H, s, —NCH$_2$), 3.73 (3H, s, OCH$_3$), 3.87 (2H, t, J 6 Hz, OCH$_2$), 4.18 (2H, q, J 7 Hz, ester CH$_2$), 5.33 (2H, s, —NCH$_2$), 6.33 (2H, m, aromatics), 6.80 (1H, m, aromatics), 7.00 (4H, ABq, Δν=39 Hz, J 9 Hz, —C$_6$H$_4$OCH$_3$), 7.16 (1H, m, aromatics), 7.28 (4H, s, C$_6$H$_4$—Cl). Mass Spec. Observed mass 619.2572, theoretical mass 619.2561 (C$_{33}$H$_{38}$ClN$_5$O$_5$).

Found: C; 63.35; H, 6.30; N, 11.30; C$_{33}$H$_{38}$ClN$_5$O$_5$ requires; C; 63.91, H, 6.18, N, 11.29%.

EXAMPLE 3

5-{3-{3-[4-(4-Chlorobenzyl)-1-piperazinyl]propoxy}phenoxy}-1-(4-methoxybenzyl)-1,2,3-triazole-4-carboxylic acid Ethyl 5-{3-{3-[4-(4-chlorobenzyl)-1-piperazinyl]propoxy}phenoxy}-1-(4-methoxybenzyl)-1,2,3-triazole-4-carboxylate, (8.00 g, 0.013 mole) was dissolved in ethanol, (150 ml) and water (50 ml) and sodium hydroxide (0.520 g, 0.013 mole) dissolved in water (5 ml) was added. The solution was stirred at room temperature for 5 hours. The reaction was neutralized with dilute hydrochloric acid and excess ethanol evaporated in vacuo. The aqueous solution was extracted with EtOAc, (three times), then chloroform (three times), and the organic extracts combined, dried (MgSO$_4$), and evaporated in vacuo to a pale yellow foam. Trituration with diethyl ether gave a white solid which was filtered off and dried in vacuo to yield 92% of the title compound, mp (EtOH) 100°-2° C. (dec). $v_{max}$ (mull) 1515, 1590, 1615, 3390 cm$^{-1}$ δ(DMSOd$_6$) 1.81 (2H, m, CH$_2$), 2.50 (10H, m, piperazinyl+CH$_2$), 3.45 (2H, s, CH$_2$N—) 3.70 (3H, s, OCH$_3$), 3.89 (2H, t, J 6 Hz, OCH$_2$), 4.75 (1H, bs, OH, exchangeable D$_2$O), 5.35 (2H, s, N—CH$_2$), 6.40 (2H, m, aromatics), 6.67 (1H, dd, J2, 8 Hz, aromatic), 7.00 (4H, ABq, Δ$v$ 84 Hz, J 9 Hz, C$_6$H$_4$OCH$_3$), 7.19 (1H, t, J 8 Hz, aromatic) 7.32 (4H, ABq, $\overline{\Delta v}$ 17 Hz, J 8.5 Hz, —C$_6$-H$_4$—Cl). Mass spec. Observed mass 547.2342, theoretical mass 547.2350 (C$_{31}$H$_{34}$ClN$_5$O$_5$—CO$_2$).

Found: C, 60.88; H, 5.63; N, 11.16; Cl, 5.47; C$_{31}$H$_{34}$ClN$_5$O$_5$.1H$_2$O requires; C, 61.02; H, 5.95; N, 11.48; Cl, 5.81%.

EXAMPLE 4

6-{3-[4-(4-Chlorobenzyl)-1-piperazinyl]-propoxy}-3-(4-methoxybenzyl)-9-oxo-9H-benzopyrano[2,3-d]-1,2,3-triazole 5-{3-{3-[4-(4-Chlorobenzyl)-1-piperazinyl]-propoxy} phenoxy}-1-(4-methoxybenzyl)-1,2,3-triazole-4-carboxylic acid, (0.50 g, 0.84 mmole), was dissolved in dry dichloromethane (20 ml) and oxalyl chloride, (1.00 ml, 11.7 mmole), added, followed by 1 drop of dimethylformamide. The reaction was stirred overnight, then excess oxalyl chloride and solvent evaporated in vacuo. The acid chloride was resuspended in dry dichloromethane, (20 ml), under nitrogen and cooled with stirring in an ice bath. A 25% solution of ethyl aluminium dichloride in hexane, (1.61 ml, 3.38 mmole) was added dropwise and the reaction stirred in ice for 2 hours, warmed to room temperature over 1 hour, and stirred for a further 3 hours. The mixture was quenched with dilute hydrochloric acid, (50 ml) and left to stand overnight. The resultant cream solid was filtered, stirred in water, (25 ml), and neutralized to pH7 with dilute sodium hydrogen carbonate solution. The aqueous phase was decanted and the gummy residue purified by column chromatography using silica gel, eluting with chloroform to give the title compound as a colourless oil which crystallized on trituration with methanol. 171 mg (35%) mp (MeOH) 135°-138° C. $v_{max}$ (mull) 1518, 1535, 1565, 1620, 1680 cm$^{-1}$ δ(CDCl$_3$) 2.00 (2H, m, CH$_2$), 2.50 (10H, bs, piperazinyl+CH$_2$), 3.43 (2H, s, N—CH$_2$), 3.77 (3H, s, OCH$_3$), 4.13 (2H, t, J 6 Hz, OCH$_2$), 5.56 (2H, s, N—CH$_2$), 6.93 (2H, m, aromatics), 7.12 (4H, ABq, Δ$v$ 45 Hz, J 9 Hz, C$_6$H$_4$OCH$_3$), 7.29 (4H, s, C$_6$H$_4$Cl) 8.28 (1H, d, J 9 Hz, aromatic).

Found: C, 64.77; H, 5.56; N, 12.16; Cl, 6.10; C$_{31}$H$_{32}$ClN$_5$O$_2$ requires; C, 64.85; H, 5.62; N, 12.20; Cl, 6.18%.

EXAMPLE 5

6-{3-[4-(4-Chlorobenzyl)-1-piperazinyl]-propoxy}-9-oxo 1H,9H-benzopyrano[2,3-d]-1,2,3-triazole The carboxylic acid from example 3 (150 mg, 0.25 mmole), was converted to its acid chloride using the same procedure as described. The acid chloride was suspended in dry dichloromethane, (10 ml), and the mixture stirred at −20° C. Aluminium chloride, (127 mg, 0.95 mmole), was added portionwise to the mixture and stirring continued for 2 hours at −20° C. The reaction was warmed to 0° C. over 1 hour, then stirred for 2 hours at 0° C., then quenched with dilute hydrochloric acid, (20 ml). After standing overnight the mixture was decanted and the residual orange gum was washed with a little water and triturated with hot methanol. Filtration of the cooled mixture gave 20 mg (16%) of the title compound as its hydrochloride. The free base was obtained by suspending the solid in water, neutralizing to pH 7 with dilute sodium hydrogen carbonate solution and filtering off the pale orange solid. After drying in vacuo 14 mg (12%) of the title compound was isolated.

Melting point and mixed melting point identical with that previously described in European Pat. No. 34,004.

EXAMPLE 6

6-{3-[4-(4-Chlorobenzyl)-1-piperazinyl]-propoxy}-9-oxo-1H,9H-benzopyrano[2,3-d]-1,2,3-triazole 6-{3-[4-(4-Chlorobenzyl)-1-piperazinyl]propoxy}-3-(4-methoxybenzyl)-9-oxo-9H-benzopyrano[2,3-d]-1,2,3-triazole (100 mg) was stirred at 40° C. in trifluoroacetic acid (2 ml) for 1.5 hours and the resulting solution was evaporated to dryness in vacuo. Water was added to the residue followed by dilute aqueous sodium bicarbonate to pH 7. The supernatant was decanted and the residual yellow gum washed by decantation with water. After drying the product was boiled with ethyl acetate to give 20 mg (25%) of title compound of mp 215°-216° C., identical spectroscopically with that prepared in EP No. 34,004.

EXAMPLE 7

6-{3-[4-(4-chlorobenzyl)-1-piperazinyl]-propoxy}-9-oxo-1H,9H-benzopyrano[2,3-d]-1,2,3-triazole The carboxylic acid from example 3 (10.0 g, 16.89 mmol) was dissolved in dry dichloromethane (450 ml) and thionyl chloride (2.742, 20.27 mmole) was added together with 10 drops of N,N-dimethylformamide. The mixture was refluxed with stirring for 4 hours under nitrogen and the solvent and excess thionyl chloride were removed in vacuo. Fresh dichloromethane (500 ml) was added and the freshly ground anhydrous aluminium chloride (7.88 g, 59.1 mmole, 3.5 equiv.) was added in three portions (over 20 minutes) at room temperature whilst under nitrogen. After a further 30 minutes the supernatant was separated from the brown oil which separated and 2M hydrochloric acid was added (250 ml). Trituration afforded a white solid which was partitioned between water and dichloromethane. Evaporation of the dried organic phase afforded crude title compound which after silica gel chromatography gave 2.68 g (35%) of material identical with that previously described in European Pat. No. 34,004.

EXAMPLE 8

6-{3-[4-(4-chlorobenzyl)-1-piperazinyl]-propoxy}-9-oxo-1H,9H-benzopyrano[2,3-d]-1,2,3-triazole The carboxylic acid from example 3 (10.0 g, 16.89 mmole) was added to polyphosphoric acid (200 ml) and the mixture was stirred for 4 hours at 110° C. under nitrogen. After cooling, the reaction was quenched with ice/water (1000 ml) and the precipitated red solid filtered off. The solid was partitioned between water and dichloromethane and the dried organic phase evaporated to give 7.5 g of crude product. Chromatography afforded 2.22 g (29%) of title compound identical to that previously prepared in European Pat. No. 34,004.

We claim:

1. A process for preparing a compound of formula (I)

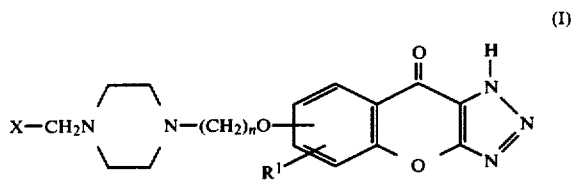

wherein X is phenyl optionally substituted by one halogen, $C_{1-4}$ alkyl or $C_{1-4}$ alkoxy; or pyridyl; $R_1$ is hydrogen or $C_{1-6}$ alkyl; and n is an integer of from 1 to 6; which process comprises, cyclising a compound of formula (II):

(II)

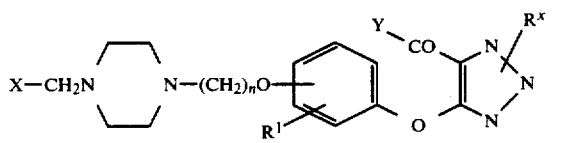

wherein X, $R^1$ and n are as defined in relation to formula (I); Y is an hydroxy or an acid activating group and $R^x$ is hydrogen or an N-protecting group and thereafter if desired carrying out one or more of the following steps: (i) removing any protecting group $R^x$, (ii) preparing a salt of the compound of formula (I).

2. A process according to claim 1 wherein in the compound of formula (II), Y is an acid activating group.

3. A process according to claim 2 wherein Y is halide.

4. A process according to claim 3 wherein Y is chloride.

5. A process according to claim 2 wherein the cyclisation is carried out in the presence of a Lewis acid.

6. A process according to claim 5 wherein the Lewis acid is aluminium trichloride or a $C_{1-6}$ alkyl aluminium dichloride.

7. A process according to claim 6 wherein the Lewis acid is aluminium trichloride.

8. A process according to claim 6 wherein the Lewis acid is ethyl aluminium dichloride.

9. A process according to claim 1 wherein in the compound of formula (II) Y is a hydroxy group.

10. A process according to claim 9 wherein the cyclisation is effected in the presence of a dehydrating agent.

11. A process according to claim 10 wherein the dehydrating agent is polyphosphoric acid or methanesulphonic acid containing phosphorus pentoxide.

12. A process according to claim 11 wherein the dehydrating agent is polyphosphoric acid.

13. A process according to any one of the preceeding claims for the preparation of a compound of formula (I)'

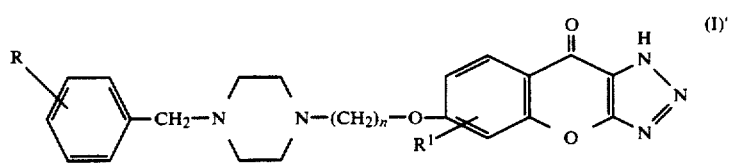

wherein R is hydrogen, halogen, $C_{1-4}$ alkyl or $C_{1-4}$ alkoxy; $R^1$ is hydrogen or $C_{1-6}$ alkyl; and n is 1 to 6.

14. A process according to any one of claims 1 to 12 for the preparation of a compound of formula (I)''

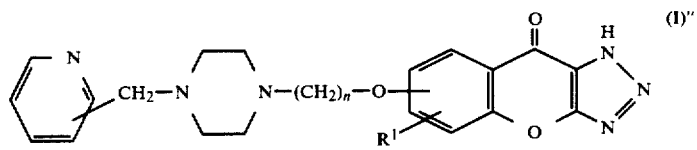

wherein $R^1$ is hydrogen or $C_{1-6}$ alkyl; and n is 1 to 6.

15. A process according to any one of claims 1 to 12 for the preparation of a compound of formula I'''

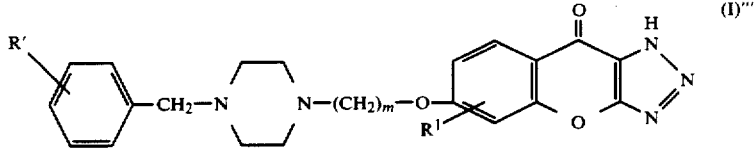

wherein R' is hydrogen or halogen, $R^1$ is hydrogen or $C_{1-6}$ alkyl or m is 2, 3 or 4.

16. A process according to claim 1 for the preparation of 6-(3-[4-(4-chlorobenzyl)-1-piperazinyl]propoxy)-9-oxo-1H,9H-benzopyrano[2,3-d]-1,2,3-triazole.

17. A compound of formula II (II)

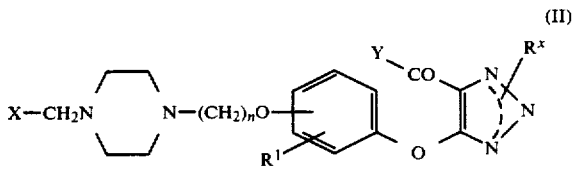

wherein X is phenyl optionally substituted by one halogen, $C_{1-4}$ alkyl or $C_{1-4}$ alkoxy; or pyridyl; $R^1$ is hydrogen or $C_{1-6}$ alkyl; n is an integer of from 1 to 6; COY is an acid, acid halide or anhydride and $R^x$ is hydrogen or $C_{2-6}$ alkoxy substituted benzyl group.
18. A compound of formula (III)
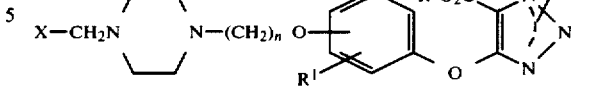
wherein X, $R^1$, $R^x$ and n are as defined in claim 17 and $R^3$ is to $C_{1-6}$ alkyl or benzyl.
* * * * *

UNITED STATES PATENT AND TRADEMARK OFFICE
CERTIFICATE OF CORRECTION

PATENT NO. : 4,692,526

DATED : September 8, 1987

INVENTOR(S) : Derek R. Buckle; Stephen T. Carpenter

It is certified that error appears in the above-identified patent and that said Letters Patent is hereby corrected as shown below:

Claim 17, line 9 reading "$C_{2-6}$ alkoxy substituted benzyl group" should read -- $C_{1-6}$ alkoxy substituted benzyl group --.

Signed and Sealed this

Twenty-eighth Day of June, 1988

Attest:

DONALD J. QUIGG

Attesting Officer

Commissioner of Patents and Trademarks